(12) United States Patent
Biener

(10) Patent No.: US 6,287,548 B1
(45) Date of Patent: Sep. 11, 2001

(54) TREATMENT OF ACNE, SEBORRHEIC DERMATITIS AND OTHER SKIN DISEASES WITH SALT SOLUTION CONTAINING NACL

(75) Inventor: Hans F. Biener, Munich (DE)

(73) Assignee: Bio.Life International AG, Zug (CH)

( * ) Notice: Subject to any disclaimer, the term of this patent is extended or adjusted under 35 U.S.C. 154(b) by 0 days.

(21) Appl. No.: 08/342,614

(22) Filed: Nov. 21, 1994

(30) Foreign Application Priority Data

Nov. 22, 1993 (DE) .................................................. 43 39 750
Nov. 22, 1993 (DE) .................................................. 43 39 751

(51) Int. Cl.[7] .......................... A61K 7/075; A61K 33/04; A61K 33/06; A61K 33/14
(52) U.S. Cl. ......................... 424/70.8; 424/70.1; 424/602; 424/606; 424/663; 424/678; 424/679; 424/680; 424/681; 424/682; 424/686; 424/687; 424/696; 424/697; 424/709; 424/715; 424/723; 514/859; 514/861; 514/863; 514/864; 514/944
(58) Field of Search .................................. 424/70.1, 70.8, 424/602, 606, 663, 678–682, 686, 687, 696, 697, 709, 715, 723; 514/859, 861, 863, 864, 944

(56) References Cited

U.S. PATENT DOCUMENTS 4,743,442  5/1988  Raaf et al. .............................. 424/47
4,943,432  7/1990  Biener ..................................... 424/47

FOREIGN PATENT DOCUMENTS 3-240730 * 10/1991 (JP) .

OTHER PUBLICATIONS

Wyngaarden, et al. (Wyngarrden), "Cecil Textbook of Medicine" W.B. Saunders Co., vol. 2, 18th Edition, p. 2321 (1988).*

* cited by examiner

Primary Examiner—Robert E. L. Sellers
(74) Attorney, Agent, or Firm—Perman & Green, LLP

(57) ABSTRACT

The present invention provides a composition of matter which has been demonstrated to be a very effective treatment for acne, seborrheic dermatitis and related skin diseases when applied to and contacted with affected skin areas, while avoiding the disadvantages and complications attendant to more established treatments. The composition comprises a synthetic mixture of salts which, when dissolved in a solvent such as water, is ionically composed primarily of a mixture of sodium and magnesium cations and chloride and sulfate anions, and which is preferably free of added zinc. More specifically, the salt mixture according to the present invention comprises the following range of composition in grams/kilogram of salt mixture in the ionic state, the balance being water of hydration:

I.

| CATIONS (g/kg salt mixture) | | ANIONS (g/kg salt mixture) | |
|---|---|---|---|
| Sodium | 150 to 380 | Chloride | 150 to 750 |
| Magnesium | 10 to 90 | Sulfate | 20 to 200 |
| Calcium | 1 to 30 | Hydrogen Carbonate | 1 to 5 |
| Potassium | 0.5 to 35 | Carbonate | 0.1 to 2 . |

28 Claims, No Drawings

TREATMENT OF ACNE, SEBORRHEIC DERMATITIS AND OTHER SKIN DISEASES WITH SALT SOLUTION CONTAINING NACL

BACKGROUND OF THE INVENTION

1. Field of the Invention

The invention concerns a topical skin preparation for the treatment of acne, seborrheic dermatitis and other skin diseases.

2. Description of Related Art

Acne is a well known and common skin disease. It has very different forms as well as grades of severity, from the so-called "pubertary pimples" i.e., a simple acne vulgaris, extending to the more dangerous forms such as acne conglobate, which can lead to severe disfigurements of the skin. It is estimated that about one quarter of all young people in the industrialized countries suffer from acne with a culmination age at 15–18 years. The disease acne seems to be generally on the increase. According to a Swiss study, the percentage of acne patients at the University Hospital of Basle increased by ten times from 1920 to 1980. While the maximum age formerly was 25 years, acne patients 50 years of age are as common today. Women of advanced age are clearly affected stronger than men. It can be assumed that the reason is the increasing stress of the skin by environmental influences and improper cosmetics.

Since acne generally is not life endangering and is regarded by some as a kind of pubertary consequence, only a small part of the people with acne have regular medical treatment. Yet a significant percentage of the population is plagued by this disease. Both disregarding it, as well as excessive and improper treatment, can lead to irreversible scars and changes of the skin, and consequent adverse effects to quality of life.

To a large extent, the aforementioned is also true for seborrheic dermatitis and other skin diseases in their different forms such as herpes, from simple irritations of the skin up to severe and irreversible changes of epidermis. For distinguishing of these diseases and in order to define their grade, dermatology uses defined terms which can be measured or counted to a high degree. Acne in its different forms such as acne aestivalis, fulminans, necroticans, cosmetica etc. is mostly defined by papules, pustules, blackheads and whiteheads, while seborrheic dermatitis and related skin diseases are generally characterized by itching, scales and erythema.

There are basically two possibilities for the therapy of acne, seborrheic dermatitis and other related skin diseases: Topical (exterior) treatment and oral treatment which is effective via the metabolism. The oral treatment is principally used only for very severe forms of acne, since retinoids and related active agents may have very strong side effects. In addition, women are endangered during their pregnancy. But even the topical remedies used up to now are not totally safe when applied at the concentration necessary for the desired therapeutic effect. Antibiotic preparations, mainly used for fighting secondary infections, are generally subject to prescription. In addition, benzoylperoxide, which is the topical remedy most used, is by no means as harmless as it would be desirable for at least the treatment of young people. In addition to its suspected carcinogenic effect established in tests with animals, it is very aggressive, and its main effect consists of the oxidation of the upper skin layers like a chemical scalpel, thereby chemically isolating these layers and causing irritation. The same applies for salicylic acid which is used to dissolve the skin by its keratolytic effect. Generally it can be stated that up to now no remedy is available with both good efficacy and skin tolerability.

It is known that salt solutions can have manifold, mainly positive effects on the skin. Well-known is the shrinking of the skin in ocean water when swimming for a long time, which is caused by osmotic effects. In some cases, upon frequent bathing in sea water, a slight reduction of acne and less itching with seborrheic dermatitis have been observed. This therapeutic effect, however, is negligibly weak and limited to isolated cases.

The effect of the Dead Sea waters on psoriasis has been therapeutically proven since ancient times. In connection with this treatment, spontaneous healings of acne have also been observed, but in a much too small number to justify such treatment.

In U.S. Pat. No. 4,943,432, a synthetic salt mixture for the treatment of psoriasis is described. This salt mixture has the following preferred ionic composition:

| | | | |
|---|---|---|---|
| Magnesium | 20–285 | Chloride | 20–750 |
| Sodium | 11–266 | Bromide | 0.2–29 |
| Calcium | 2–235 | Sulfate | 0.2–22 |
| Potassium | 2–95 | Borate | 0.05–14 |
| Strontium | 0.02–10.5 | Silicate | 0.02–14 |
| Iron | 0.02–8.5 | Fluoride | 0.001–11 |
| Aluminum | 0.001–6.0 | Iodide | 0.001–9.5 |
| Zinc | 0.001–2.5 | Carbonate | 0.0002–9.0 |
| Lithium | 0.001–2.0 | Hydrogen-carbonate | 0.0001–8.5 |

Psoriasis is treated with extremely good results using this salt mixture, either as a bath solution or topically applied in the form of a gel. Yet, therapeutic practice has shown that, contrary to the good healing effect on psoriasis, other skin diseases such as acne and seborrheic dermatitis are not influenced as much as would be desired.

Testing has established that, contrary to psoriasis, the effect of the salt mixtures described in the above-mentioned patents was statistically ineffective for treatment of acne and seborrheic dermatitis with a bathing treatment. When such a salt mixture was used gelified with cellulose ether, it also proved to be statistically ineffective for treatment of these conditions.

Accordingly, an object of the invention is to provide a salt mixture composition for the treatment of acne, seborrheic dermatitis and other related skin diseases which, contrary to the treatments known so far, combines a high specific efficacy while avoiding overall adverse effect to the skin and physiology.

SUMMARY OF THE INVENTION

The present invention provides a composition of matter which has been demonstrated to be an effective treatment for acne, seborrheic dermatitis and related skin diseases when applied to and contacted with affected skin areas, while avoiding the disadvantages and complications attendant to established treatments as described above. The composition comprises a synthetic mixture of salts which, when dissolved in a solvent such as water, is ionically composed primarily of a mixture of sodium and magnesium cations and chloride and sulfate anions, and which is preferably free of added Zinc. More specifically, the salt mixture according to the present invention comprises the following approximate range of composition in grams/kilogram of salt mixture in the ionic state, the balance being water of hydration:

| I. | CATIONS (g/kg) | | ANIONS (g/kg) | |
|---|---|---|---|---|
| | Sodium | 150 to 380 | Chloride | 150 to 750 |
| | Magnesium | 10 to 90 | Sulfate | 20 to 200 |
| | Calcium | 1 to 30 | Hydrogen Carbonate | 1 to 5 |
| | Potassium | 0.5 to 35 | Carbonate | 0.1 to 2 |

The composition may be applied to the affected areas of the skin as a solution, i.e., as a bath, moist swab or spray, or more preferably in combination with a suitable application medium such as to form a gel, salve, shampoo or a liquid or solid soap.

The invention also provides a method for treating skin diseases comprising topically applying to the affected skin areas a therapeutic salt composition solution comprising a mixture of:

a) from about 1 to 30% by weight of a salt composition containing, in the ionic state, a mixture comprising sodium, magnesium, calcium, potassium, chloride, sulfate, hydrogen carbonate and carbonate ions, said ions constituting at least about 97.5% by weight of the ionic content of said salt composition;

b) from about 0.05 to about 10% by weight of a therapeutic agent at least partially soluble in said solution and effective for treatment of said skin disease; and c) a solvent for said salt composition.

DETAILED DESCRIPTION OF THE INVENTION

The composition of the present invention may be characterized as being essentially free of organic impurities such as bitumens, oil tars, sewage residues and organic residues as are found in natural salt solutions, e.g., Dead Sea waters. The composition may be further characterized as composed primarily, e.g., at least about 97.5% by weight (exclusive of water of hydration), of a mixture of water soluble salts including sodium chloride, calcium chloride or sulfate, potassium chloride or sulfate, magnesium chloride or sulfate, sodium hydrogen carbonate and sodium carbonate, each mixed in suitable proportions to give rise to compositions having a formulation in the ionic state as described above. In a more preferred embodiment of the invention, the salt mixture is of the formula above and also includes a source of strontium ions, e.g., strontium chloride and/or a source of bromide ions, e.g., sodium bromide such that at least about 99.5% by weight of the mixture (exclusive of water of hydration) has the following composition in grams/kilogram in the ionic state:

| CATIONS (g/kg salt mixture) | | ANIONS (g/kg salt mixture) | |
|---|---|---|---|
| Sodium | 267 to 320 | Chloride | 450–to 600 |
| Magnesium | 30 to 40 | Sulfate | 60–120 |
| Calcium | 5 to 15 | Hydrogen Carbonate | 3–4.2 |
| Potassium | 6 to 14 | Bromide | 1–2.5 |
| Strontium | 0.1 to 0.3 | Carbonate | 0.3–0.7 |

The salt mixtures of this invention differ in a number of important respects from those described in U.S. Pat. No. 4,943,432 discussed above. Most notable is the higher content of sodium and sulfate ions and lower content of magnesium and calcium ions associated with the mixtures of the present invention. In addition, the mixture of the present invention is preferably free of added Zinc, and more preferably is also free of added iodide, fluoride, silicate, borate, lithium, aluminum and iron ions which contribute to the efficacy of salt mixtures used to treat psoriasis but which, for reasons not presently understood, have been found to be of no therapeutic effect and even detract from the efficacy of salt mixtures used to treat skin disorders such as acne and seborrheic dermatitis.

In a more preferred embodiment of the invention, the content of sodium chloride constitutes at least about 50% by weight of the salt mixture, more preferably at least about two thirds (67%) by weight of the mixture and the content of sodium ions in the mixture is preferably in excess of 270 grams/kilogram of salt mixture, more preferably in the range of from about 275 to 300 grams/kilogram of salt mixture. It has been found that as a result of the inclusion of sodium in the composition at these levels, the therapeutic effect with respect to acne and seborrheic dermatitis increases dramatically while the therapeutic effect towards psoriasis is found to decrease.

The salt mixtures of the invention are most conveniently applied to the skin as a solution dissolved in a suitable solvent such as water, a lower alcohol or a polyol such as glycerol, or a mixture of two or more of these. Preferably the solvent is distilled or deionized water, which may also contain an alcohol or a water soluble polyol such as glycerol, alone or combined with a suitable carrier or application medium such as to form a gel, an ointment, a salve, a shampoo, or a liquid or solid soap. The concentration of the salt mixture in the solvent or in the application medium will generally range from about 1 to about 30% by weight, more preferably from about 2 to about 15% by weight and most preferably from about 2.5 to about 12% by weight.

Gels or ointment compositions may be conveniently prepared by mixing the salt solution with from about 0.5 to 3% by weight of a natural or synthetic gum or gelling colloid additives as are known in the art, and permitting the mixture to gel. Particularly preferred gelling additives are cellulose esters or ethers. Such compositions may also contain up to about 30% by weight of other additives such as lanolin or glycerin which provide a smooth feel to the skin. Shampoos and soaps may be prepared by formulating the salt solutions with conventional shampoo or soap ingredients, e.g., surface active agents such as ionic or non-ionic surfactants, fatty alcohols, builders, quaternary ammonium salts, fatty esters and fatty amides normally used in such compositions. These compositions may also contain other additives such as preservatives, dyes, perfumes and like conventional additives.

In addition to the therapeutic effect exhibited by the compositions of this invention with respect to the treatment of acne and seborrheic dermatitis, these compositions also demonstrate a remarkable absorbency by the skin, particularly when applied as a solution or as a gel. Thus, the compositions may be used as a carrier medium for known therapeutic agents which are effective for the treatment of not only acne and seborrheic dermatitis, but also other skin conditions such as herpes or psoriasis. The therapeutic agent should be at least partially soluble in the solvent and may be dissolved in the solvent in relatively small concentrations, because it is quickly and efficiently transported into and through the skin when topically applied. Thus, any skin irritations which might occur as a side effect from application of these therapeutic agents at a higher concentration are minimized. The salt composition also produces a softening effect on the skin which tends to counteract adverse skin reactions to these therapeutics.

Conventional therapeutic anti-acne and anti-dermatitis agents which may be included in the composition include hormones, antibiotics, antiseborrhoics and anti keratotics, which are at least partially soluble in the solvent used to prepare the solution. These should be added in amounts such that any normal skin irritation which may be caused by their use is minimized, i.e, generally from about 0.05% by weight to about 10% by weight, more preferably from about 1 to 7% by weight. Examples of suitable therapeutic agents include resorcinol, ibuprofen piconol, resorcinolmonoacetate, chlorohexidine, benzoyl peroxide, salicylic acid, fumaric acid, vitamin A acid, hexachlorophene, acelainic acid, and glycyrrhetinic acid and their salts, sulfonamides, colloidal sulfur, ichthyol pyrithion, selenium derivatives, and the like, as well as antibiotics such as erythromycin or tetracyclines.

Other known active therapeutic ingredients which may be included in the composition at the above levels for the treatment of herpes and other viral infections include virustatica or viracides such as aciclovir, idoxuridin, tromantadin, podophyelotoxin, vidarabin and combinations thereof.

Still other therapeutic agents which may be included in the composition include skin conditioners such as lanolin and germ extracts.

The following examples and therapeutic data are illustrative of the invention.

EXAMPLE 1

A therapeutic composition was prepared by dry mixing the following ingredients (pharmaceutical grade):

553.4 grams Sodium chloride (NaCl)
106.3 grams Magnesium chloride ($MgCl_2$-6 $H_2O$)
92.7 grams Magnesium sulfate ($MgSO_4$)
25.8 grams Calcium chloride ($CaCl_2$-2 $H_2O$)
15.8 grams Potassium chloride (KCl)
4.1 grams Sodium hydrogencarbonate ($NaHCO_3$)
1.2 grams Sodium bromide (NaBr)
0.7 grams Sodium carbonate ($Na_2CO_3$)

A solution was formed by dissolving the above salt mixture in 9,000 mls of deionized water to provide a concentration of dissolved solids of 8% by weight. This solution was then formed into a gel by thoroughly mixing it with 1.5% by weight of Hydroxyethylcellulose and 0.07% by weight of a preservative, and permitting the resultant mixture to form a gel.

EXAMPLE 2

A shampoo was prepared by mixing the salt mixture described in Example 1 with a conventional shampoo formulation containing a mixture of anionic lauryl sulfate surfactants, cocoamide, a protein hydrolysate, a quaternary ammonium compound and water. The shampoo was adjusted to a pH of 6.0 by addition of citric acid and contained 8% by weight of dissolved inorganic salt solids.

Clinical tests were conducted as follows:
A. Acne Treatment with Gel

In a controlled study with 100 patients (average age 19.2 years; acne symptoms since an average of 4.4 years), the therapeutic efficacy of the salt gel preparation for the treatment of acne was examined. The gel preparation of Example 1 was applied as a thin layer to the skin once a day for a period of six weeks. The patients received either the salt gel (n=75) or only a placebo gel without active salt ingredients (n=25) which was not otherwise distinguishable by color or odor from the active gel. At the beginning of therapy as well as two, four and six weeks after, the number of pustules, papules, open and closed comedones was counted on each patient. After six weeks, an additional evaluation of compatibility/tolerance and efficacy was made, separately by patients and physicians.

In the Verum group, a significant reduction of the number of pustules, papules and comedones (both open and closed) was demonstrated after six weeks compared to the beginning of therapy (p=0.001); a significant improvement of the clinical status was already evident after 14 days in the Verum group (p=0.05). In the Placebo group, there were no significant improvements of the single symptoms; thus the number of pustules, papules, open and closed comedones was highly significantly lower in the Verum group than in the Placebo group after 6 weeks (p=0.001). The number of pustules, papules, open and closed comedones was reduced after 6 weeks to 9–25% of the original values in the Verum group, while the symptoms in the Placebo group remained practically unchanged with 70–99% of the original values.

For the single symptom "pustules" there was even a deterioration of the start values in the Placebo group: After 6 weeks, the number of pustules was about 120% of the original number.

In the Verum group, efficacy and compatibility/tolerance were judged to be very good or good in all cases, both by patients and physicians; in the Placebo group, both patients and physicians judged the efficacy to be poor to bad, but the compatibility/tolerance was judged to be very good.

B. Seborrheic Dermatitis Treatment with Gel

In a controlled study with 66 patients suffering from seborrheic dermatitis of varying degrees of the face and upper part of the body (average age 36 years), the therapeutic efficacy of the gel of the present invention was evaluated. The gel preparation of Example 1 was applied as a thin layer to the affected areas of the skin once a day for a period of four weeks. The patients received either the active salt gel of Example 1 (n=54) or a placebo gel without the active salt ingredients (n=12), which was not otherwise distinguishable by color or odor from the active gel. Control examinations of the affected skin areas took place at the beginning of the therapy (week 0) as well as after 2 weeks (week 2) and 4 weeks (week 4). At the beginning of the therapy as well as at the examinations after 2 and 4 weeks, the symptoms "itching", "erythema" and "scales" were defined by discreet parameters as follows: 0=none; 1=little; 2=medium and 3=severe. In addition, the percentage reduction of the sum scores of the symptoms in relation to the scores at the beginning of the therapy were evaluated. A therapeutical effect was defined when the reduction of the symptom scores fell below 50% of the value at the beginning of the therapy.

The progress of the therapy was evaluated by the change in symptoms as documented in Tables 1–3.

TABLE 1

| Time | Sum | Average Value | Sta. dev. | Test | Level |
|---|---|---|---|---|---|
| Degree of Severity of the Symptom Itching Verum Group | | | | | |
| Week 0 | 117 | 2,14 | 0,73 | W0 ag. W2 | *** |
| Week 2 | 23 | 0,43 | 0,63 | W2 ag. W4 | n.s. |
| Week 4 | 1 | 0,04 | 0,04 | W0 ag. W4 | *** |

TABLE 1-continued

| Time | Sum | Average Value | Sta. dev. | Test | Level |
|---|---|---|---|---|---|
| Degree of Severity of the Symptom Itching Placebo Group | | | | | |
| Week 0 | 28 | 2.33 | 0.62 | W0 ag. W2 | n.s. |
| Week 2 | 26 | 2.17 | 0.69 | W2 ag. W4 | n.s. |
| Week 4 | 19 | 1.58 | 1.58 | W0 ag. W4 | * |

TABLE 2

| Time | Sum | Average Value | Sta. dev. | Test | Level |
|---|---|---|---|---|---|
| Degree of Severity of the Symptom Erythema Verum Group | | | | | |
| Week 0 | 81 | 1,50 | 0,67 | W0 ag. W2 | n.s. |
| Week 2 | 54 | 1,0 | 0,51 | W2 ag. W4 | ** |
| Week 4 | 13 | 0,24 | 0,00 | W0 ag. W4 | *** |
| Degree of Severity of the Symptom Erythema Placebo Group | | | | | |
| Week 0 | 27 | 2.25 | 0.43 | W0 ag. W2 | n.s. |
| Week 2 | 27 | 2.25 | 0.43 | W2 ag. W4 | n.s. |
| Week 4 | 21 | 1.75 | 0.83 | W0 ag. W4 | n.s. |

TABLE 3

| Time | Sum | Average Value | Sta. dev. | Test | Level |
|---|---|---|---|---|---|
| Degree of Severity of the Symptom Scales Verum Group | | | | | |
| Week 0 | 62 | 1.15 | 0,45 | W0 ag. W2 | ** |
| Week 2 | 19 | 0.35 | 0,55 | W2 ag. W4 | n.s. |
| Week 4 | 3 | 0.06 | 0,23 | W0 ag. W4 | *** |
| Degree of Severity of the Symptom Scales Placebo Group | | | | | |
| Week 0 | 14 | 1.17 | 0,45 | W0 ag. W2 | n.s. |
| Week 2 | 15 | 1.25 | 0,55 | W2 ag. W4 | n.s. |
| Week 4 | 17 | 1.17 | 0,23 | W0 ag. W4 | n.s. |

Abbreviations
Sta. dev. = Standard deviation
Wx = Examination date after Week x
ag. = Against
n.s. = No significant difference
*= Significant difference, p = 0.05
**= Very significant difference, p = 0.01
***= Highly significant difference, p = 0.001

The data in Tables 1–3 show a very clear and highly significant reduction of the average values for all three symptoms in the Verum group between the beginning and end of the therapy. In contrast, the Placebo group shows no significant changes in any of these symptoms.

C. Treatment of Scalp Seborrheic Dermatitis with Shampoo

In a controlled study with 55 patents suffering from seborrheic dermatitis of the hairy scalp (average age 37.4 years), the therapeutic efficacy of the shampoo described in Example 2 was evaluated. The shampoo (8 gms) was applied to wetted hair, lathered into the scalp for a period of 2 minutes, and rinsed. This treatment was repeated once daily for a period of 4 weeks. The patients received either the active shampoo of Example 2 (n=28) or a placebo shampoo (n=27) which did not contain the active salt ingredients but was otherwise identical to the shampoo of Example 2, and which was not otherwise distinguishable by color or odor from the active shampoo. Control examinations of the affected scalp skin areas took place at the beginning of the therapy (week 0) as well as after 2 and 4 weeks as in the case of the gel study described above. These examinations were evaluated using the same criteria and standards as used in the gel evaluations described above, and test results are shown in Tables 4–6.

TABLE 4

Degree of Severity of the Single Symptoms, Verum Group.

| | ITCHING | ERYTHEMA | SCALES |
|---|---|---|---|
| Beginning of Study | | | |
| Sum Scores | 55 | 50 | 37 |
| Average Value | 1.96 | 1.82 | 1.3 |
| Standard Deviation | 0.82 | 0.77 | 0.93 |
| Week 2 | | | |
| Sum Scores | 28 | 26 | 16 |
| Average Value | 1 | 0.9 | 0.56 |
| Standard Deviation | 0.6 | 0.59 | 0.68 |
| Week 4 | | | |
| Sum Scores | 6 | 6 | 16 |
| Average Value | 0.22 | 0.22 | 0.56 |
| Standard Deviation | 0.49 | 0.49 | 0.5 |

TABLE 5

Degree of Severity of the Single Symptoms, Placebo Group.

| | ITCHING | ERYTHEMA | SCALES |
|---|---|---|---|
| Beginning of Study | | | |
| Sum Scores | 42 | 39 | 47 |
| Average Value | 1.48 | 1.3 | 1.63 |
| Standard Deviation | 0.78 | 0.67 | 0.76 |
| Week 2 | | | |
| Sum Scores | 35 | 39 | 43 |
| Average Value | 1.22 | 1.33 | 1.52 |
| Standard Deviation | 0.74 | 0.78 | 0.68 |
| Week 4 | | | |
| Sum Scores | 35 | 37 | 33 |
| Average Value | 1.22 | 1.26 | 1.19 |
| Standard Deviation | 0.63 | 0.71 | 0.47 |

TABLE 6

Course of Total Scores.

| VERUM GROUP | | | |
|---|---|---|---|
| Total Score | 142 | 70 | 28 |
| Average Value | 5.07 | 2.52 | 1 |
| Standard Deviation | 1.69 | 1.3 | 1.17 |
| PLACEBO GROUP | BEGINNING OF STUDY | WEEK 2 | WEEK 4 |
| Total Score | 128 | 117 | 105 |
| Average Value | 4.4 | 4.07 | 3.67 |
| Standard Deviation | 1.84 | 1.83 | 1.35 |

Based on the data from Tables 4–6, the Verum group showed a strong reduction of the sum scores and the average values of the total symptoms as well as the single symptoms "itching", "erythema" and "scales". The difference between beginning of the therapy and second week was already significant (probability p=0.01–0.005). Between beginning of the therapy and week 4, the difference was highly significant (probability p=0.001 or 99%).

There was no significant reduction of the sum scores and the average values in the Placebo group, neither of the general symptoms nor of the single symptoms "itching" and "erythema". Solely the symptom "scales" was less in the Placebo group, compared between start of the therapy and the fourth week. Statistical comparison of the two groups at the three examination dates shows a difference for the symptoms "itching" and "erythema" at the start of the therapy. This means that these symptoms were stronger in the randomized Verum group. Regarding the symptom "scales", there were no significant differences at the start time of the therapy, although the sum scores as well as the average values were higher in the Placebo group than in the Verum group. Yet, there was no statistically significant difference regarding the total sum scores and their average values at the beginning of the clinical study between the two groups. At the end of the study, there were highly significant lower values for all single symptoms and for the total sum scores in the Verum group compared with the Placebo group.

In no single case was there an allergic reaction or any lasting irritation observed with the patients treated with the salt compositions of this invention.

EXAMPLE 3

The gel composition of Example 1 was prepared except that about 1% by weight of salicylic acid was included in the formulation. The gel was applied and rubbed into human skin. The skin appeared dry to the touch after about 1–2 minutes, indicating that the composition had been effectively absorbed into the skin.

A control gel was prepared also containing 1% by weight of salicylic acid but without inclusion of the salt mixture described in Example 1. After application of the same quantity of the control gel to the skin, the skin remained damp even after 15 minutes, indicating poor absorption of the therapeutic into the skin.

Example 3 illustrates that the salt compositions of the present invention serve as an excellent carrier medium for therapeutic agents. Because of high absorption by the skin, the composition vanishes quickly from the skin thereby carrying the therapeutic agent with it into the skin.

What is claimed is:

1. A method for treating acne or seborrheic dermatitis skin disease comprising topically applying to the affected skin areas a therapeutic salt composition solution, said solution comprising a mixture of:
   (a) from about 1 to 30% by weight of a salt composition prepared by mixing salt components such that, in the ionic state, a mixture comprising sodium, magnesium, calcium, potassium, chloride, sulfate, hydrogen carbonate and carbonate ions is formed, said ions constituting at least about 97.5% by weight of the ionic content of said salt composition and said salt composition containing at least 50% by weight of sodium chloride; said salt composition further characterized as containing at least 60 grams/kilogram of salt mixture in the ionic state of sulfate ions;
   (b) from about 0.05 to about 10% by weight of a therapeutic agent at least partially soluble in said solution and effective for treatment of said skin disease; and
   (c) a solvent for said salt composition.

2. The method of claim 1 wherein said salt composition is free of added zinc.

3. The method of claim 1 wherein said salt mixture further contains from about 1 to 2.5 grams/kilogram of salt mixture of bromide ions.

4. The method of claim 1 wherein said salt mixture further contains from about 0.1 to 0.3 grams/kilogram of salt mixture of strontium ions.

5. A method for treating acne or seborrheic dermatitis comprising contacting the affected skin areas with a composition prepared by mixing salt components such that the salt components are present in the mixture in the following approximate proportions, expressed as grams/kilograms of salt mixture in the ionic state:

| CATIONS (g/kg) | | ANIONS (g/kg) | |
|---|---|---|---|
| Sodium | 150 to 380 | Chloride | 150 to 750 |
| Magnesium | 10 to 90 | Sulfate | 60 to 200 |
| Calcium | 1 to 30 | Hydrogen Carbonate | 1 to 5 |
| Potassium | 0.5 to 35 | Carbonate | 0.1 to 2 | said salt components comprising at least 50% by weight sodium chloride, said composition further characterized as being dissolved in a solvent and as being free of added Zinc.

6. The method of claim 5 wherein said composition further contains from about 1 to 2.5 grams/kilogram of salt mixture of bromide ions.

7. The method of claim 5 wherein said composition further contains from about 0.1 to 0.3 grams/kilogram of salt mixture of strontium ions.

8. The method of claim 5 wherein said composition is dissolved in water solvent at a concentration within the range of from about 1 to about 30% by weight.

9. A method for treating acne or seborrheic dermatitis comprising contacting the affected skin areas with a composition prepared by mixing salt components such that the salt components are present in the mixture in the following approximate proportions, expressed as grams/kilogram of salt mixture in the ionic state:

| CATIONS (g/kg) | | ANIONS (g/kg) | |
|---|---|---|---|
| Sodium | 267 to 320 | Chloride | 450 to 600 |
| Magnesium | 30 to 40 | Sulfate | 60 to 120 |
| Calcium | 5 to 15 | Hydrogen Carbonate | 3 to 4.2 |
| Potassium | 6 to 14 | Carbonate | 0.3 to 0.7 | said salt components comprising at least 50% by weight sodium chloride, said composition further characterized as being dissolved in a solvent and as being free of added Zinc.

10. The method of claim 9 which further contains from about 1 to 2.5 grams/kilogram of salt mixture of bromide ions.

11. The method of claim 9 which further contains from about 0.1 to 0.3 grams/kilogram of salt mixture of strontium ions.

12. The method of claim 9, wherein said salt mixture is dissolved in water as a carrier medium at a concentration within the range of from about 2.5 to about 12% by weight.

13. The method of claim 9 wherein said skin disease is acne.

14. The method of claim 9 wherein said skin disease is seborrheic dermatitis.

15. The method of claim 9 wherein said composition further contains surface active agents.

16. The method of claim 9 wherein said composition is also free of added iodide, fluoride, silicate, borate, lithium, aluminum and iron ions.

17. The method of claim 9 wherein said salt components of said composition comprise at least 67% by weight of sodium chloride.

18. A method for treating acne or seborrheic dermatitis skin disease comprising topically applying to the affected skin areas a therapeutic salt composition solution, said solution comprising a mixture of:

(a) from about 1 to 30% by weight of salt composition prepared by mixing salt components such that, in the ionic state, a mixture comprising sodium, magnesium, calcium, potassium, chloride, sulfate, hydrogen carbonate and carbonate ions is formed, said ions constituting at least about 97.5% by weight of the ionic content of said salt composition and said salt composition containing at least 50% by weight of sodium chloride, said salt components being present in the mixture in the following proportions, expressed as grams/kilogram of salt mixture in the ionic state:

| CATIONS (g/kg) | | ANIONS (g/kg) | |
| --- | --- | --- | --- |
| Sodium | 267 to 320 | Chloride | 450 to 600 |
| Magnesium | 30 to 40 | Sulfate | 60 to 120 |
| Calcium | 5 to 15 | Hydrogen Carbonate | 3 to 4.2 |
| Potassium | 6 to 14 | Carbonate | 0.3 to 0.7 |

(b) from about 0.05 to about 10% by weight of therapeutic agent at least partially soluble in said solution and effective for treatment of said skin disease; and (c) a solvent for said salt composition.

19. The method of claim 18 wherein said solvent comprises water.

20. The method of claim 18 wherein said salt composition is free of added Zinc.

21. The method of claim 18 wherein said composition is mixed with surface active agents sufficient to form a shampoo.

22. The method of claim 18 wherein said salt composition is also free of added iodide, fluoride, silicate, borate, lithium, aluminum and iron ions.

23. The method of claim 18 wherein said salt composition comprises at least 67% by weight sodium chloride.

24. The method of claim 18 wherein said salt composition further contains from about 1 to 2.5 grams/kilogram of salt mixture of bromide ions.

25. The method of claim 18 wherein said salt composition further contains from about 0.1 to 0.3 grams/kilogram of salt mixture of strontium ions.

26. The method of claim 18 wherein said salt composition is dissolved in water at a concentration within the range of from about 2.5 to about 12% by weight.

27. The method of claim 18 wherein said skin disease is acne.

28. The method of claim 18 wherein said skin disease is seborrheic dermatitis.

* * * * *